United States Patent [19]

Alt et al.

[11] Patent Number: 4,567,299

[45] Date of Patent: Jan. 28, 1986

[54] HERBICIDAL 2-HALOACETANILIDES

[75] Inventors: Gerhard H. Alt, University City; James S. Bannon, St. Louis, both of Mo.

[73] Assignee: Monsanto Company, St. Louis, Mo.

[21] Appl. No.: 685,872

[22] Filed: Dec. 24, 1984

[51] Int. Cl.[4] ..................... C07C 103/34; A01N 37/18
[52] U.S. Cl. ....................................... 564/214; 71/118
[58] Field of Search ........................... 564/214; 71/118

[56] References Cited

U.S. PATENT DOCUMENTS 3,403,994 10/1968 Olin ................................. 564/214 X
3,404,976 10/1968 Olin ................................. 564/214 X
3,475,157 10/1969 Olin ................................. 564/214 X

*Primary Examiner*—Paul F. Shaver
*Attorney, Agent, or Firm*—William I. Andress

[57] ABSTRACT

The disclosure herein relates to a group of N-methyl-2-haloacetanilide compounds, herbicidal compositions containing said compounds as the active ingredient and herbicidal method of use in various crops, particularly soybeans. The herbicides herein are particularly effective against the hard-to-kill annual weeds Texas panicum, itchgrass, wild proso millet, alexandergrass, shattercane and seedling johnsongrass.

12 Claims, No Drawings

HERBICIDAL 2-HALOACETANILIDES

BACKGROUND OF THE INVENTION

1. Field of the Invention

This invention pertains to the field of 2-haloacetanilides and their use in the agronomic arts, e.g., as herbicides.

2. Description of the Prior Art

The prior art relevant to this invention includes numerous disclosures of 2-haloacetanilides which may be unsubstituted or substituted with a wide variety of substituents on the anilide nitrogen atom and on the anilide ring including alkyl, alkoxy, alkoxyalkyl, halogen, etc., radicals.

As relevant to the present invention, wherein the compounds are substituted with specific alkyl radical combinations on the anilide nitrogen and in both ortho positions of the anilide ring, the prior art discloses a limited number of certain homologs or isomers. While said prior art compounds may control certain acetamide-sensitive weeds, they are not known to be particularly effective in the control of various acetamide-resistant weeds, such as the annual grasses Texas panicum, raoulgrass (itchgrass), wild proso millet, alexandergrass, shattercane and seedling johnsongrass.

It is an object of this invention to provide herbicides which selectively control hard-to-kill annual weeds such as those mentioned above, while also controlling or suppressing a broad spectrum of less-resistant perennial and annual weeds, while maintaining crop safety in various crops, especially soybeans.

SUMMARY OF THE INVENTION

The present invention relates to herbicidally active compounds, herbicidal compositions containing these compounds as active ingredients and herbicidal method of use of said compositions in various crops.

It has now been found that a selective group of 2-haloacetanilides characterized by specific combinations of alkyl radicals on the anilide nitrogen atom and in both ortho positions of the anilide ring possess unexpectedly superior and outstanding herbicidal properties relative to the most-closely-related compounds of the most relevant prior art.

A primary feature of the herbicidal compositions of this invention is their ability to control a wide spectrum of weeds, including weeds controllable by current herbicides and, additionally, a plurality of weeds which, individually and/or collectively, have heretofore escaped control, while maintaining crop safety with respect to certain crops, particularly, soybeans.

While prior art herbicides are useful for controlling a variety of weeds, including on occasion certain resistant weeds, the unique herbicides of this invention have been found to be capable of controlling or greatly suppressing a plurality of resistant weeds, most notably annual weeds, such as Texas panicum, itchgrass, wild proso millet (*Panicum miliaceum*), alexandergrass, shattercane and seedling johnsongrass, while controlling and/or suppressing other less-resistant perennial and annual weeds.

In more particular, the compounds of this invention are those having the formula

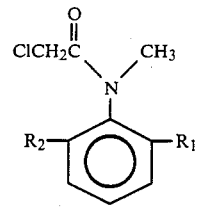

wherein $R_1$ is n-butyl or sec-butyl and $R_2$ is methyl or ethyl, provided that when $R_1$ is n-butyl, $R_2$ is methyl.

The compounds of particular utility disclosed and claimed herein, which correspond to the above formula are 2-chloro-2'-n-butyl-N,6'-dimethyl acetanilide, 2-chloro-2'-sec-butyl-N,6'-dimethyl acetanilide and 2-chloro-2'-sec-butyl-6'-ethyl-N-methyl acetanilide.

The herbicidal compositions herein are useful as selective herbicides by applying them to the locus of undesirable plants to be controlled and desirable plants to be protected, including particularly soybeans.

The invention will be more clearly understood by reference to the following detailed description. The compounds according to this invention are suitably prepared by known processes, e.g., by N-alkylation of secondary amides under basic conditions in the presence of a phase transfer catalyst as described in U.S. Pat. No. 4,258,196. The alkylating agent may be used per se or made in situ. Similarly, the secondary amide starting material is prepared by known means, e.g., the chloroacetylation of the appropriate primary amine. Alternatively, compounds according to this invention may be prepared according to the process described in U.S. Pat. No. 3,475,157, which process involves the chloroacetylation of the appropriate secondary aniline, which, itself, may be prepared by reacting the appropriate secondary aniling substituted in just one ortho position with an alkyl halide, e.g., methyl iodide, to introduce the alkyl group into the second ortho position.

DETAILED DESCRIPTION OF THE INVENTION

Example 1

This example describes the preparation of 2-chloro-2'-n-butyl-N,6'-dimethyl acetanilide.

To a mixture of 5.0 g (0.021 mole) of 2-chloro-2'-n-butyl-6'-methyl acetanilide, 2.9 g (0.023 mole) of dimethyl sulfate and 2.0 g of benzyltriethylammonium chloride in 100 ml of $CH_2Cl_2$ was added 80 ml of 50% NaOH with stirring for about 40 minutes. Water, 150 ml, cooled in an ice bath was added, the formed organic layer separated, extracted with water, dried over $MgSO_4$ and evaporated. A brown liquid, b.p. 115° C. at 0.2 mg Hg was obtained in the amount of 4.5 g (85% yield).

Anal. calc'd for $C_{14}H_{20}ClNO$ (percent); Theory: C, 66.25; H, 7.96; Cl, 13.97, N, 5.52; Found: C, 66.15; H, 7.99; N, 5.57.

The product was identified as 2-chloro-2'-n-butyl-N,6'-dimethyl acetanilide.

Example 2

To a mixture of 5.2 g (0.02 mole) of 2-chloro-2'-sec-butyl-6'-ethyl acetanilide, 2.8 g (0.022 mole) of dimethyl sulfate and 2.0 g of benzyltriethylammonium chloride in 200 ml of $CH_2Cl_2$ chilled to 5° C. was added 20 ml of 50% NaOH with stirring for 5 minutes. Water, 150 ml, was added, the formed organic layer separated, extracted with water, dried over MgSO$_4$ and evaporated. A clear oil, b.p. 120° C. at 0.07 mg Hg (Kugelrohr), was obtained in the amount of 3.8 g (72% yield).

Calc'd for C$_{15}$H$_{22}$ClNO (percent); Theory: C, 67.28; H, 8.28; Cl, 13.24; N, 5.23; Found: C, 67.16; H, 8.31; Cl, 13.22.

The product was identified as 2-chloro-2'-sec-butyl-6'-ethyl-N-methyl acetanilide.

Example 3

To a mixture of 6.3 g (0.026 mole) of 2-chloro-2'-sec-butyl-6'-methyl acetanilide, 3.4 g (0.026 mole) of dimethyl sulfate and 2.6 g of benzyltriethylammonium chloride in 250 ml of CH$_2$Cl$_2$ chilled to 5° C. was added 26 ml of 50% NaOH with stirring for 10 minutes. Water, 150 ml, was added, the formed organic layer separated, extracted with water, dried over MgSO$_4$ and evaporated. A clear oil, b.p. 112° C. at 0.05 mg Hg (Kugelrohr), was obtained in the amount of 5.1 g (76% yield).

Calc'd for C$_{14}$H$_{20}$ClNO (percent): Theory: C, 66.26; H, 7.94; Cl, 13.97; N, 5.52; Found: C, 66.21; H, 7.94; Cl, 13.96

The product was identified as 2-chloro-2'-sec-butyl-N,6'-dimethyl acetanilide.

Example 4

As mentioned above, the secondary anilides used as starting materials in the N-alkylation process used in the above examples are prepared by known methods, e.g., haloacetylation of the corresponding aniline. For example, the starting sec-anilide used in Example 3 was prepared as follows:

2-sec-butyl-6-ethyl aniline, 0.1 mole in 100 ml of toluene were added to 20 ml of toluene containing 0.105 moles of chloroacetyl chloride and heated at reflux for 10 hours. The mixture was cooled, some of the solvent stripped and hexane added. The product crystallized and was filtered, washed with hexane and dried in air to yield 18 g m.p. 85°–88° C.

The product was identified as 2-chloro-2'-sec-butyl-6'-ethyl acetanilide.

As noted above, the compounds of this invention have been found to be effective as herbicides, particularly as pre-emergence herbicides.

In order to illustrate benefits of the activity of the compounds of this invention, the preemergence herbicidal activity of the compounds of this invention was determined in greenhouse tests on selected plants.

The pre-emergence data were obtained as follows:

A good grade of top soil is placed in aluminum pans and compacted to a depth of three-eighths to one-half inch (0.95–1.27 cm) from the top of the pan. On the top of the soil is placed a number of seeds or vegetative propagules of various plant species. The soil required to level fill the pans after seeding or adding vegetative propagules is weighed into a pan. The soil and a known amount of the active ingredient applied in a solvent or as a wettable powder suspension are thoroughly mixed, and used to cover the prepared pans. After preparation the pans are then watered by subirrigation as needed to give adequate moisture for germination and growth. Observations are made about 2–3 weeks after seeding and treatment.

Tables I and II summarize results of tests conducted to determine the preemergence herbicidal activity of the compounds of this invention. The herbicidal rating was obtained by means of a fixed scale based on the percent injury of each plant species. The ratings are defined as follows:

| % Inhibition | Rating |
|---|---|
| 0–24 | 0 |
| 25–49 | 1 |
| 50–74 | 2 |
| 75–100 | 3 |

The plant species utilized in one set of tests, the data for which are shown in Table I, are identified by letter in accordance with the following legend:

| | | | | | |
|---|---|---|---|---|---|
| A | Canada Thistle, rhizome | E | Lambsquarters, common | I | Johnsongrass, rhizome |
| B | Cocklebur | F | Smartweed, Pennsylvania | J | Downy Brome |
| C | Velvetleaf | G | Yellow Nutsedge, tubers | K | Barnyardgrass |
| D | Morningglory | H | Quackgrass, rhizome | | |

TABLE I

Pre-Emergence Herbicidal Activity

| Compound of Example No. | Rate (kg/ha) | Plant Species | | | | | | | | | |
|---|---|---|---|---|---|---|---|---|---|---|---|
| | | A | B | C | D | E | F | G | H | I | J | K |
| 1 | 11.2 | 3 | 2 | 1 | 3 | 3 | 3 | 3 | 3 | 2 | 3 | 3 |
|   | 5.6  | 3 | 2 | 1 | 3 | 3 | 3 | 3 | 3 | 0 | 3 | 3 |
| 2 | 11.2 | 3 | 2 | 2 | 3 | 3 | 3 | 3 | 3 | 3 | 3 | 3 |
|   | 5.6  | 3 | 2 | 1 | 2 | 3 | 3 | 3 | 3 | 3 | 3 | 3 |
| 3 | 11.2 | 3 | 1 | 3 | 3 | 3 | 3 | 3 | 3 | 3 | 3 | 3 |
|   | 5.6  | 3 | 0 | 3 | 3 | 3 | 3 | 3 | 3 | 3 | 3 | 3 |

The compounds were further tested by utilizing the above procedure on the following plant species:

| | | | | |
|---|---|---|---|---|
| L | Soybean | R | Hemp Sesbania |
| M | Sugarbeet | E | Lambsquarters, common |
| N | Wheat | F | Smartweed, Pennsylvania |
| O | Rice | C | Velvetleaf |
| P | Sorghum | J | Downy Brome |
| B | Cocklebur | S | Panicum Spp. |
| Q | Wild Buckwheat | K | Barnyardgrass |
| D | Morningglory | T | Crabgrass, large |

The results are summarized in Table II.

TABLE II

Pre-Emergence Herbicidal Activity

| Compound of Example No. | Rate (kg/ha) | Plant Species | | | | | | | | | | | | | | |
|---|---|---|---|---|---|---|---|---|---|---|---|---|---|---|---|---|
| | | L | M | N | O | P | B | Q | D | R | E | F | C | J | S | K | T |
| 1 | 5.6    | 2 | 3 | 3 | 3 | 3 | 2 | 2 | 3 | 3 | 3 | 3 | 2 | 3 | 3 | 3 | 3 |
|   | 1.12   | 0 | 3 | 3 | 3 | 2 | 1 | 1 | 3 | 3 | 2 | 3 | 1 | 3 | 3 | 3 | 3 |
|   | 0.28   | 0 | 1 | 2 | 2 | 0 | 0 | 1 | 0 | 1 | 2 | 1 | 0 | 1 | 3 | 3 | 3 |
|   | 0.056  | 0 | 0 | 0 | 1 | 0 | 0 | 0 | 0 | 2 | 1 | — | 0 | 0 | 2 | 3 | 3 |
|   | 0.0112 | 0 | 0 | 0 | 0 | 0 | — | 0 | 0 | 2 | 1 | — | 0 | 0 | 0 | 1 | 2 |

TABLE II-continued

| Compound of Example No. | Rate (kg/ha) | Pre-Emergence Herbicidal Activity Plant Species | | | | | | | | | | | | | | |
|---|---|---|---|---|---|---|---|---|---|---|---|---|---|---|---|---|
| | | L | M | N | O | P | B | Q | D | R | E | F | C | J | S | K | T |
| 2 | 5.6 | 2 | 3 | 3 | 3 | 3 | 2 | 3 | 2 | 3 | 3 | 3 | 2 | 3 | 3 | 3 | 3 |
|   | 1.12 | 0 | 3 | 3 | 3 | 3 | 1 | 2 | 2 | 3 | 2 | 1 | 0 | 3 | 3 | 3 | 3 |
|   | 0.28 | 1 | 2 | 1 | 1 | 3 | 0 | 2 | 0 | 2 | 2 | 2 | 0 | 3 | 3 | 3 | 3 |
|   | 0.056 | 0 | 1 | 0 | 0 | 1 | 0 | 0 | 1 | 2 | 1 | — | 0 | 2 | 3 | 3 | 3 |
|   | 0.0112 | 0 | 1 | 0 | 0 | 0 | 0 | 0 | 0 | 1 | 0 | 0 | 0 | 1 | 1 | 3 | 3 |
| 3 | 5.6 | 3 | 3 | 3 | 3 | 3 | 0 | 3 | 3 | 3 | 3 | 3 | 3 | 3 | 3 | 3 | 3 |
|   | 1.12 | 1 | 3 | 3 | 3 | 3 | 0 | 3 | 3 | 3 | 3 | 3 | 2 | 3 | 3 | 3 | 3 |
|   | 0.28 | 1 | 3 | 3 | 2 | 3 | 0 | 3 | 1 | 3 | 3 | 2 | 1 | 3 | 3 | 3 | 3 |
|   | 0.056 | 1 | 3 | 1 | 1 | 1 | 0 | 1 | 0 | 1 | 2 | 2 | 0 | 2 | 3 | 3 | 3 |
|   | 0.0112 | 1 | 2 | 0 | 0 | 0 | 0 | 0 | 0 | 1 | 1 | 0 | 0 | 1 | 2 | 2 | 2 |

The herbicides of this invention have been found to possess unexpectedly superior properties as pre-emergence herbicides, most particularly in the selective control of the hard-to-kill annual weeds, Texas panicum, seedling johnsongrass, shattercane, alexandergrass, wild proso millet, and itchgrass, while also controlling or suppressing many other less-resistant perennial and annual weeds.

Selective control and increased suppression of the above-mentioned weeds with the invention herbicides have been found particularly effective in soybeans.

In order to illustrate the unexpectedly superior properties of the compounds of this invention both on an absolute basis and on a relative basis, comparative tests were conducted in the greenhouse with compounds of the prior art most closely related in chemical structure to the invention compounds.

Those compounds of the prior art (see identification below) which have a methyl radical on the nitrogen atom, a methyl or ethyl radical in one ortho position and a butyl radical in the other ortho position are deemed to be structurally more similar to the invention compounds than other compounds having other alkyl chain lengths in the nitrogen and ortho positions. Compound I is included, less for structural similarity to the invention compounds (because it contains an isopropyl radical on the nitrogen atom and no ring substituents), than the fact that it is propachlor, active ingredient in the commercial herbicide RAMROD ®.

In the comparative tests below, the data from which is recorded in Tables III–V, the prior art compounds are identified by letter symbol as follows:

A. 2-chloro-2'-t-butyl-6'-methyl-N-methyl acetanilide (Ex. 69, U.S. Pat. No. 3,442,945).
B. 2-chloro-2'-t-butyl-6'-ethyl-N-methyl acetanilide (U.S. Pat. No. 3,442,945; no specific example).
C. 2-chloro-2'-t-butyl-6'-methyl-N-ethyl acetanilide (Ex. 70, U.S. Pat. No. 3,442,945).
D. 2-chloro-2'-t-butyl-6'-methyl-N-isobutyl acetanilide (Ex. 79, U.S. Pat. No. 3,442,945).
E. 2-chloro-N,2',6'-trimethyl acetanilide (Examples 8 and 16, U.S. Pat. No. 4,258,196).
F. 2-chloro-2'-ethyl-N,6'-dimethyl acetanilide (U.S. Pat. No. 3,442,945; no specific example).
G. 2-chloro-2',6'-diethyl-N-methyl acetanilide (U.S. Pat. No. 3,442,945; no specific example).
H. 2-chloro-N-isopropyl acetanilide (U.S. Pat. No. 2,863,752; no specific example).

In the discussion of data below, reference is made to herbicide application rates symbolized as "$GR_{15}$" and "$GR_{85}$"; these rates are given in kilograms per hectare (kg/ha) which are convertible into pounds per acre (lbs/A) by dividing the kg/ha rate by 1.12. $GR_{15}$ defines the maximum rate of herbicide required to produce 15% or less crop injury, and $GR_{85}$ defines the minimum rate required to achieve 85% inhibition of weeds. The $GR_{15}$ and $GR_{85}$ rates are used as a measure of potential commercial performance, it being understood, of course, that suitable commercial herbicides may exhibit greater or lesser plant injuries within reasonable limits.

A further guide to the effectiveness of a chemical as a selective herbicide is the "selectivity factor" ("SF") for a herbicide in given crops and weeds. The selectivity factor is a measure of the relative degree of crop safety and weed injury and is expressed in terms of the $GR_{15}/GR_{85}$ ratio, i.e., the $GR_{15}$ rate for the crop divided by the $GR_{85}$ rate for the weed, both rates in kg/ha (lb/A). In the tables below, selectively factors are shown in parenthesis following the $GR_{85}$ rate for each weed; the symbol "NS" indicates "non-selective"; the symbol "ND" means "not determined".

Since crop tolerance and weed control are interrelated, a brief discussion of this relationship in terms of selectivity factors is meaningful. In general, it is desirable that crop safety factors, i.e., herbicide tolerance values, be high, since higher concentrations of herbicide are frequently desired for one reason or another and tolerance to such higher concentrations is indicative of excellent crop safety. Conversely, it is desirable that weed control rates be small, i.e., the herbicide possesses high unit activity, for economical and possibly ecological reasons. However, small rates of application of a herbicide may not be adequate to control certain weeds and a larger rate may be required. Hence the best herbicides are those which control the greatest number of weeds with the least amount of herbicide and provide the greatest degree of crop safety, i.e., crop tolerance. Accordingly, use is made of "selectivity factors" (defined above) to quantify the relationship between crop safety and weed control. With reference to the selectivity factors listed in the tables, the higher the numerical value, the greater selectivity of the herbicide for weed control in a given crop.

In the comparative test below, greenhouse preemergence herbicidal activity data are presented, first in Table III comparing the relative efficacy of the compound of Examples 1–3 herein, with the most relevant compounds of the prior art, viz., Compounds A and B, as selective herbicides against particular weeds commonly associated with soybeans. The test data in Tables III–VI below for all compounds was obtained under head-to-head identical test conditions, i.e., surface application of the herbicide followed by an initial overhead irrigation, then by subirrigation as necessary. The data represent the averages of two replicate runs for each compound. The weeds used in the tests herein have the following abbreviations in the tables: Texas panicum (TP), seedling johnsongrass (SJG), shattercane (SC), alexandergrass (AG), wild proso millet (WPM), fall panicum (FP), red rice (RR) and itchgrass (IG).

isomeric t-butyl radical in one ortho position. The data from this head-to-head comparison is shown in Table IV.

TABLE III

| Com- pound | GR$_{15}$ Rate (Kg/Ha) Soybean | PREEMERGENCE HERBICIDAL ACTIVITY GR$_{85}$ Rate (kg/Ha) | | | | | | | |
|---|---|---|---|---|---|---|---|---|---|
| | | TP | SJG | SC | AG | WPM | FP | RR | IG |
| Ex. 1 | 2.24 | 0.56(4.0) | 0.56(4.0) | 0.14(16.0) | 0.25(~9.0) | 0.28(8.0) | <0.14(>16.0) | >2.24(NS) | 1.12(2.0) |
| Ex. 2 | 2.24 | 0.14(16.0) | <0.14(>16.0) | <0.14(>16.0) | 0.38(5.9) | 0.56(4.0) | <0.14(>16.0) | >2.24(NS) | 0.14(16.0) |
| Ex. 3 | 2.24 | 0.14(16.0) | <0.14(>16.0) | <0.14(>16.0) | 0.38(5.9) | 0.28(8.0) | <0.14(>16.0) | >2.24(NS) | <0.14(>16) |
| A | 0.75 | 1.12(NS) | 0.38(~2.0) | 0.42(1.8) | 0.56(1.3) | 2.24(NS) | <0.14(>5.4) | >2.24(NS) | 0.42(1.8) |
| B | >2.24 | 1.12(>2.0) | 0.28(>8.0) | 0.28(>8.0) | 0.38(>5.9) | 0.84(>2.7) | <0.14(>16.0) | >2.24(ND) | 0.38(>5.9) |

TABLE IV

| Com- pound | GR$_{15}$ Rate (Kg/Ha) Soybean | PREEMERGENCE HERBICIDAL ACTIVITY GR$_{85}$ Rate (kg/Ha) | | | | | | | |
|---|---|---|---|---|---|---|---|---|---|
| | | TP | SJG | SC | AG | WPM | FP | RR | IG |
| Ex. 1 | 2.24 | 0.56(4.0) | 0.56(4.0) | 0.14(16.0) | 0.25(~9.0) | 0.28(8.0) | <0.14(>16.0) | >2.24(NS) | 1.12(2.0) |
| Ex. 2 | 2.24 | 0.14(16.0) | <0.14(>16.0) | <0.14(>16.0) | 0.38(5.9) | 0.56(4.0) | <0.14(>16.0) | >2.24(NS) | 0.14(16.0) |
| Ex. 3 | 2.24 | 0.14(16.0) | <0.14(>16.0) | <0.14(>16.0) | 0.38(5.9) | 0.28(8.0) | <0.14(>16.0) | >2.24(NS) | <0.14(>16) |
| C | 2.24 | >2.24(NS) | 2.24(1.0) | 1.12(2.0) | 0.88(2.6) | >2.24(NS) | 1.12(2.0) | >2.24(NS) | 2.24(1.0) |
| D | >2.24 | >2.24(NS) | >2.24(NS) | >2.24(NS) | >2.24(NS) | >2.24(NS) | >2.24(NS) | >2.24(NS) | >2.24(NS) |

Reference to the data in Table III will show that each of the invention compounds exhibited significantly higher safety factors (GR$_{15}$ rates) in soybeans, generally higher unit activity against weeds (GR$_{85}$ rates) and selectivity factors than Compound A, which was non-selective in Texas panicum, wild proso millet and red rice (as were all test compounds within the test limits).

As compared with Compound B, the more active prior art compound, the compounds of the invention had comparable safety in soybeans up to the maximum test rate and generally higher unit activity against most weeds. In more particular, ignoring the indeterminable comparison against red rice, the compound of Example 1 exhibited superior unit activity in four of the eight weeds (TP, SC, AG and WPM), comparable unit activity in FP and less unit activity against only two weeds, SJG and IG, compared to both prior art compounds A and B.

A comparison of prior art compounds A and B with those of Examples 2 and 3 shows that Examples 2 and 3 exhibited higher unit activity than A against all test weeds, except FP and RR in which the activities were comparable. Moreover, Examples 2 and 3 also exhibited higher unit activities than B against all test weeds except AG, FP and RR wherein the activities of all compounds were comparable.

In yet another comparison, the invention compounds were compared under identical test conditions with other compounds of the prior art differing therefrom in having higher homologous alkyl radical radicals on the nitrogen atom, e.g., ethyl or isobutyl and having the Referring to the data in Table IV, it is readily apparent that prior art Compound D was essentially herbicidally inactive against the test weeds within the test limits; that prior art Compound C was non-selective against the weeds TP, WPM and RR and, otherwise, markedly inferior to each of the invention compounds as selective herbicides against all of the test weeds in soybeans.

In still another head-to-head comparison, the invention compounds were compared against prior art compounds which, similarly as the invention compounds have a methyl radical on the anilide nitrogen and a methyl or ethyl radical in one ortho position of the anilide ring, but, unlike the invention compounds, have a methyl or ethyl radical in the other ortho position (whereat the invention compounds have a n-butyl or sec-butyl radical. The test data for this comparison is set forth in Table V.

TABLE V

| Com- pound | GR$_{15}$ Rate (Kg/Ha) Soybean | PREEMERGENCE HERBICIDAL ACTIVITY GR$_{85}$ Rate (kg/Ha) | | | | | | | |
|---|---|---|---|---|---|---|---|---|---|
| | | TP | SJG | SC | AG | WPM | FP | RR | IG |
| Ex. 1 | 2.24 | 0.56(4.0) | 0.56(4.0) | 0.14(16.0) | 0.25(~9.0) | 0.28(8.0) | <0.14(>16.0) | >2.24(NS) | 1.12(2.0) |
| Ex. 2 | 2.24 | 0.14(16.0) | <0.14(>16.0) | <0.14(>16.0) | 0.38(5.9) | 0.56(4.0) | <0.14(>16.0) | >2.24(NS) | 0.56(4.0) |
| Ex. 3 | 2.24 | 0.14(16.0) | <0.14(>16.0) | <0.14(>16.0) | 0.38(5.9) | 0.28(8.0) | <0.14(>16.0) | >2.24(NS) | <1.14(>16) |
| E | 2.24 | >2.24(NS) | 1.12(>3.0) | 2.24(1.0) | 2.10(1.1) | <2.24(NS) | 0.14(16.0) | ~2.0(~1.1) | >2.24(NS) |
| F | >2.24 | 1.68(>1.3) | 0.56(>4.0) | 0.50(>4.5) | 0.84(>2.7) | 1.12(>2.0) | <0.14(>16.0) | 1.9(>1.2) | 1.68(>1.3) |
| G | >2.24 | 2.24(>1.0) | 0.56(>4.0) | 0.56(>4.0) | 0.50(>4.5) | 0.47(>4.8) | <0.14(>16.0) | 0.89(>2.5) | 0.89(>2.5) |

Reference to the data in Table V will show that with few exceptions, the invention compounds had generally outstandingly superior unit activities vis-a-vis the prior art compounds against the test weeds in soybeans. Fall panicum (FP) is a relatively acetamide-sensitive weed, hence, it is expected that this weed would suffer high injury with all acetanilide test compounds. With respect to said exceptions, the prior art compounds had slightly higher unit activities than the invention compounds only against red rice. Compound G was slightly more active than compound of Example 1 against itchgrass and slightly more active than to the compound of Example 2 against wild proso millet.

In a final comparison, the invention compounds were compared under identical conditions for preemergence herbicidal activity against propachlor, active ingredient in the commercial herbicide RAMROD®, the only commercial acetanilide herbicide having an alkyl substituent on the anilide nitrogen atom.

The comparative test data involving propachlor is shown in Table VI. It is immediately apparent that propachlor did not control any of the test weeds at rates up to the maximum test rate of 2.24 kg/ha, the actual $GR_{85}$ (and $GR_{15}$) rates being at some indeterminate value above 2.24 kg/ha. Each of the invention compounds exhibited high-unit activity against all test weeds, except red rice, and soybean safety of at least 2.24 kg/ha, thus resulting in very high selectivity factors within the test rates.

TABLE VI

| | | PREEMERGENCE HERBICIDAL ACTIVITY | | | | | | | |
|---|---|---|---|---|---|---|---|---|---|
| Com- | $GR_{15}$ Rate (Kg/Ha) | | | | $GR_{85}$ Rate (kg/Ha) | | | | |
| pound | Soybean | TP | SJG | SC | AG | WPM | FP | RR | IG |
| Ex. 1 | 2.24 | 0.56(4.0) | 0.56(4.0) | 0.14(16.0) | 0.25(~9.0) | 0.28(8.0) | <0.14(>16.0) | >2.24(NS) | 1.12(2.0) |
| Ex. 2 | 2.24 | 0.14(16.0) | <0.14(>16.0) | <0.14(>16.0) | 0.38(5.9) | 0.56(4.0) | <0.14(>16.0) | >2.24(NS) | 0.56(4.0) |
| Ex. 3 | 2.24 | 0.14(16.0) | <0.14(>16.0) | <0.14(>16.0) | 0.38(5.9) | 0.28(8.0) | <0.14(>16.0) | >2.24(NS) | <0.14(>16) |
| H | >2.24 | >2.24(ND) | >2.24(ND) | >2.24(ND) | >2.24(ND) | >2.24(ND) | >2.24(ND) | >2.24(ND) | >2.24(ND) |

The herbicidal compositions of this invention including concentrates which require dilution prior to application contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The compositions of this invention, particularly liquids and wettable powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl, naphthalene sulfonates, sodium naphthalene sulfonate, and the polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powder compositions of this invention usually contain from about 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts of inert solid extender, all parts being by weight of the total composition. Where required, from about 0.1 to 2.0 parts of the solid inert extender can be replaced by a corrosion inhibitor of anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring an aqueous mixture of a water-insoluble active ingredient and an emulsification agent until uniform and then homogenized to give stable emulsion of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

In another form of aqueous suspensions, a water-immiscible herbicide is encapsulated to form microencapsulated phase dispersed in an aqueous phase. In one embodiment, minute capsules are formed by bringing together an aqueous phase containing a lignin sulfonate emulsifier and a water-immiscible chemical and polymethylene polyphenylisocyanate, dispersing the water-immiscible phase in the aqueous phase followed by addition of a polyfunctional amine. The isocyanate and amine compounds react to form a solid urea shell wall around particles of the water-immiscible chemical, thus forming microcapsules thereof. Generally, the concentration of the microencapsulated material will range from about 480 to 700 g/l of total composition, preferably 480 to 600 g/l.

Concentrates are usually solutions of active ingredient in water-immiscible or partially water-immiscible solvents together with a surface active agent. Suitable solvents for the active ingredient of this invention include dimethylformide, dimethylsulfoxide, N-methylpyrrolidone, hydrocarbons and water-immiscible ethers, esters or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts preferably from about 3 to 20 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivatives, thiolcarbamates, triazoles, benzoic acids, nitriles, biphenyl ethers and the like such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a:2',1'-c)-pyrazidiinium salt
5-Bromo-3-isopropyl-6-methyluracil
1,1'-Dimethyl-4,4'-bipyridinium

Ureas

N'-(4-chlorophenoxy)phenyl-N,N-dimethylurea
N,N-dimethyl-N'-(3-chloro-4-methylphenyl)urea
3-(3,4-dichlorophenyl)-1,1-dimethylurea
1,3-Dimethyl-3-(2-benzothiazolyl)urea
3-(p-Chlorophenyl)-1,1-dimethylurea
1-Butyl-3-(3,4-dichlorophenyl)-1-methylurea

Carbamates/Thiolcarbamates

2-Chloroallyl diethyldithiocarbamate
S-(4-chlorobenzyl)N,N-diethylthiolcarbamate
Isopropyl N-(3-chlorophenyl)carbamate
S-2,3-dichloroallyl N,N-diisopropylthiolcarbamate
Ethyl N,N-dipropylthiolcarbamate
S-propyl dipropylthiolcarbamate

Acetamides/Acetanilides/Anilines/Amides

2-Chloro-N,N-diallylacetamide
N,N-dimethyl-2,2-diphenylacetamide
N-(2,4-dimethyl-5-[[(trifluoromethyl)sulfonyl]amino]phenyl)acetamide
N-Isopropyl-2-chloroacetanilide
2',6'-Diethyl-N-methoxymethyl-2-chloroacetanilide
2'-Methyl-6'-ethyl-N-(2-methoxyprop-3-yl)-2-chloroacetanilide
α,α,α-Trifluoro-2,6-dinitro-N,N-dipropyl-p-toluidine
N-(1,1-dimethylpropynyl)-3,5-dichlorobenzamide

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
Sodium 5-[2-chloro-4-(trifluoromethyl)phenoxy]-2-nitrobenzoate
4,6-Dinitro-o-sec-butylphenol
N-(phosphonomethyl)glycine and its $C_{1-6}$ monoalkyl amine and alkaline metal salts and combinations thereof
2-[4,5-Dihydro-4-methyl-4-(1-methylethyl)-5-oxo-1H-imidazol-2-yl]-3-quinolinecarboxylic acid
Benzoic acid, 2-((([(4-Chloro-6-Methoxy-2-pyrimidinyl)amino]carbonyl)amino)sulfonyl)-, ethyl ester

Ethers 2,4-Dichlorophenyl-4-nitrophenyl ether
2-Chloro-α,α,α-trifluoro-p-tolyl-3-ethoxy-4-nitrodiphenyl ether

Miscellaneous 2,6-Dichlorobenzonitrile
Monosodium acid methanearsonate
Disodium methanearsonate Fertilizers useful in combination with the active ingrediente include, for example, ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

|  | Weight Percent |
|---|---|
| I. Emulsifiable Concentrates (EC's) | |
| A. Compound of Example No. 1 | 35.6 |
| Calcium dodecylbenzene sulfonate/polyoxyethylene ethers blend (e.g., Atlox ® 3437F) | 5.0 |
| Monochlorobenzene | 29.7 |
| C$_9$ aromatic hydrocarbon | 29.7 |
|  | 100.00 |
| B. Compound of Example No. 2 | 85.0 |
| Calcium dodecyl sulfonate/alkylaryl polyether alcohol blend | 4.0 |
| C$_9$ aromatic hydrocarbons solvent | 11.0 |
|  | 100.00 |
| C. Compound of Example No. 3 | 5.0 |
| Calcium dodecylbenzene sulfonate/polyoxyethylene ethers blend (e.g., Atlox 3437F) | 1.0 |

-continued

| | Weight Percent |
|---|---|
| Xylene | 94.0 |
| | 100.00 |
| II. Liquid Concentrates | |
| A. Compound of Example No. 1 | 10.0 |
| Xylene | 90.0 |
| | 100.00 |
| B. Compound of Example No. 2 | 85.0 |
| Dimethyl sulfoxide | 15.0 |
| | 100.00 |
| C. Compound of Example No. 3 | 50.0 |
| N—methylpyrrolidone | 50.0 |
| | 100.00 |
| D. Compound of Example No. 1 | 5.0 |
| Ethoxylated castor oil | 20.0 |
| Rhodamine B | .5 |
| Dimethyl formamide | 74.5 |
| | 100.00 |
| III. Emulsions | |
| A. Compound of Example No. 2 | 40.0 |
| Polyoxyethylene/polyoxy-propylene block copolymer with butanol (e.g., Tergitol ® XH) | 4.0 |
| Water | 56.0 |
| | 100.00 |
| B. Compound of Example No. 3 | 5.0 |
| Polyoxyethylene/polyoxy-propylene block copolymer with butanol | 3.5 |
| Water | 91.5 |
| | 100.00 |
| IV. Wettable Powders | |
| A. Compound of Example No. 1 | 25.0 |
| Sodium lignosulfonate | 3.0 |
| Sodium N—methyl-N—oleyl-taurate | 1.0 |
| Amorphous silica (synthetic) | 71.0 |
| | 100.00 |
| B. Compound of Example No. 2 | 80.0 |
| Sodium dioctyl sulfosuccinate | 1.25 |
| Calcium lignosulfonate | 2.75 |
| Amorphous silica (synthetic) | 16.00 |
| | 100.00 |
| C. Compound of Example No. 3 | 10.0 |
| Sodium lignosulfonate | 3.0 |
| Sodium N—methyl-N—oleyl-taurate | 1.0 |
| Kaolinite clay | 86.0 |
| | 100.00 |
| V. Dusts | |
| A. Compound of Example No. 1 | 2.0 |
| Attapulgite | 98.0 |
| | 100.00 |
| B. Compound of Example No. 2 | 60.0 |
| Montmorillonite | 40.0 |
| | 100.00 |
| C. Compound of Example No. 1 | 30.0 |
| Bentonite | 70.0 |
| | 100.00 |
| D. Compound of Example No. 3 | 1.0 |
| Diatomaceous earth | 99.0 |
| | 100.00 |
| VI. Granules | |
| A. Compound of Example No. 1 | 15.0 |
| Granular attapulgite (20/40 mesh) | 85.0 |
| | 100.00 |
| B. Compound of Example No. 2 | 30.0 |
| Diatomaceous earth (20/40) | 70.0 |
| | 100.00 |
| C. Compound of Example No. 2 | 0.5 |
| Bentonite (20/40) | 99.5 |
| | 100.00 |
| D. Compound of Example No. 3 | 5.0 |
| Pyrophyllite (20/40) | 95.0 |
| | 100.00 |
| VII. Microcapsules | |
| A. Compound of Example No. 1 encapsulated in polyurea shell wall | 49.2 |

-continued

| | Weight Percent |
|---|---|
| Sodium lignosulfonate (e.g. Reax 88B ®) | 0.9 |
| Water | 49.9 |
| | 100.00 |
| B. Compound of Example No. 2 encapsulated in polyurea shell wall | 10.0 |
| Potassium lignosulfonate (e.g., Rexas C-21 ®) | .5 |
| Water | 89.5 |
| | 100.00 |
| C. Compound of Example No. 3 encapsulated in polyurea shell wall | 80.0 |
| Magnesium salt of lignosulfate (Treax LTM ®) | 2.0 |
| Water | 18.0 |
| | 100.00 |

When operating in accordance with the present invention, effective amounts of the acetanilides of this invention are applied to the soil containing the plants, or are incorporated into aquatic media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The application of an effective amount of the compounds of this invention to the locus of undesired weeds is essential and critical for the practice of the present invention. The exact amount of active ingredient to be employed is dependent upon various factors, including the plant species and stage of development thereof, the type and condition of soil, the amount of rainfall and the specific acetanilide employed. In selective preemergence application to the plants or to the soil a dosage of from 0.02 to about 11.2 kg/ha, preferably from about 0.04 to about 5.60 kg/ha, or suitably from 1.12 to 5.6 kg/ha of acetanilide is usually employed. Lower or higher rates may be required in some instances. One skilled in the art can readily determine from this specification, including the above example, the optimum rate to be applied in any particular case.

The term "soil" is employed in its broadest sense to be inclusive of all conventional "soils" as defined in Webster's New International Dictionary, Second Edition, Unabridged (1961). Thus the term refers to any substance or media in which vegetation may take root and grow, and includes not only earth but also compost, manure, muck, humus, sand and the like, adapted to support plant growth.

Although the invention is described with respect to specific modifications, the details thereof are not to be construed as limitations except to the extent indicated in the following claims.

We claim:

1. Compounds having the formula

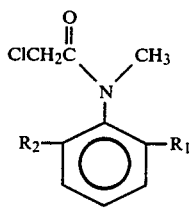

wherein $R_1$ is n-butyl or sec-butyl and $R_2$ is methyl or ethyl, provided that when $R_1$ is n-butyl, $R_2$ is methyl.

2. Compound according to claim 1 which is 2-chloro-2'-n-butyl-N,6'-dimethyl acetanilide.

3. Compound according to claim 1 which is 2-chloro-2'-sec-butyl-6'-ethyl-N-methyl acetanilide.

4. Compound according to claim 1 which is 2-chloro-2'-sec-butyl-N,6'-dimethyl acetanilide.

5. Herbicidal compositions comprising an inert adjuvant and a herbicidally-effective amount of a compound having the formula

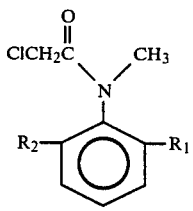

wherein $R_1$ is n-butyl or sec-butyl and $R_2$ is methyl or ethyl, provided that when $R_1$ is n-butyl, $R_2$ is methyl.

6. Compound according to claim 5 wherein said compound is 2-chloro-2'-n-butyl-N,6'-dimethyl acetanilide.

7. Compound according to claim 5 wherein said compound is 2-chloro-2'-sec-butyl-6'-ethyl-N-methyl acetanilide.

8. Compound according to claim 5 wherein said compound is 2-chloro-2'-sec-butyl-N,6'-dimethyl acetanilide.

9. Method for controlling undesirable vegetation which comprises applying to the locus thereof a herbicidal composition comprising an inert adjuvant and a herbicidally-effective amount of a compound having the formula

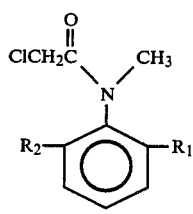

wherein $R_1$ is n-butyl or sec-butyl and $R_2$ is methyl or ethyl, provided that when $R_1$ is n-butyl, $R_2$ is methyl.

10. Method according to claim 9 wherein said compound is 2-chloro-2'-n-butyl-N,6'-dimethyl acetanilide.

11. Method according to claim 9 wherein said compound is 2-chloro-2'-sec-butyl-6'-ethyl-N-methyl acetanilide.

12. Method according to claim 9 wherein said compound is 2-chloro-2'-sec-butyl-N,6'-dimethyl acetanilide.

* * * * *